United States Patent
Gutsche et al.

(10) Patent No.: US 6,245,727 B1
(45) Date of Patent: Jun. 12, 2001

(54) DISCONTINUOUS PROCESS FOR CONDUCTING A HETEROGENEOUSLY CATALYZED REACTION AND INSTALLATION FOR HETEROGENEOUSLY CATALYZED MANUFACTURE OF PRODUCTS

(75) Inventors: Bernhard Gutsche; Lutz Jeromin; Eberhard Peukert, all of Hilden; Levent Yueksel, Duesseldorf; Kurt Adrian, St. Augustin-Hangelar; Heinz Bollweg, St. Augustin-Birlinghoven, all of (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 08/259,362

(22) Filed: Jun. 14, 1994

Related U.S. Application Data

(63) Continuation of application No. 07/761,810, filed on Sep. 20, 1991, now abandoned.

(30) Foreign Application Priority Data

Mar. 20, 1989 (DE) .................................................. 39 09 128
Mar. 12, 1990 (WO) .................................. PCT/EP90/00398

(51) Int. Cl.[7] .................................................. C07C 43/30
(52) U.S. Cl. ............................................................ 508/591
(58) Field of Search ............................................. 568/591

(56) References Cited

U.S. PATENT DOCUMENTS 5,110,508 * 5/1992 Buettgen et al. ..................... 554/170

FOREIGN PATENT DOCUMENTS

| 3813612 | 11/1989 | (DE) . |
| 3826320 | 2/1990 | (DE) . |
| 0178669 | 4/1986 | (EP) . |
| 0342357 | 11/1989 | (EP) . |
| 2185613 | 1/1974 | (FR) . |
| 2293238 | 8/1976 | (FR) . |
| 1526977 * | 10/1978 | (GB) . |

* cited by examiner

*Primary Examiner*—James H. Reamer
(74) *Attorney, Agent, or Firm*—John E. Drach; Henry E. Millson, Jr.

(57) ABSTRACT

The invention relates firstly to a discontinuous process for conducting a heterogeneously catalyzed reaction taking place at elevated temperature, in which heat-sensitive products are formed, a heat transfer unit (4) different from the reactor (1) being used for heating and a fixed-bed catalyst (3) being used as the catalyst and the reaction mixture being continuously circulated in succession through the catalyst (3) and then through the heat transfer unit (4). The problem to be solved in this process is to avoid losses of catalyst and product and to shorten the batch time and, optionally, the reaction time in accordance with German patent applications P 38 13 612.0 and P 38 26 320.3.

The invention also relates to a plant for the discontinuous heterogeneously catalyzed production of heat-sensitive products at elevated temperature comprising a reactor (1), characterized by a heat transfer unit (4) arranged outside and connected to the reactor (1), a catalyst container (3) containing a fixed-bed catalyst preceding the heat transfer unit and a pump (2) for continuously circulating the reaction mixture in succession through the catalyst (3) and then through the heat transfer unit (4).

11 Claims, 2 Drawing Sheets

DISCONTINUOUS PROCESS FOR CONDUCTING A HETEROGENEOUSLY CATALYZED REACTION AND INSTALLATION FOR HETEROGENEOUSLY CATALYZED MANUFACTURE OF PRODUCTS

This application is a continuation, Ser. No. 07/761,810 filed on Sep. 20, 1991 now abandoned.

This invention relates to a discontinuous process for conducting a heterogeneously catalyzed reaction taking place at elevated temperature, in which heat-sensitive products are formed.

In discontinuous processes for conducting heterogeneously catalyzed reactions, solid catalysts directly introduced into the reactor are size-reduced by stirring elements and have to be filtered after the reaction. This often gives rise to considerable losses of catalyst and product. Another problem arises where it is intended to take the measures described in German patent applications P 38 13 612.0 and P 38 26 320.3 to shorten the batch time and, optionally, the reaction time. In this case, problems arise during circulation of the solids-laden reaction mixture, particularly at the liquid distributor of the film evaporator.

The problem addressed by the present invention on the one hand is to avoid the losses of catalyst and product in a process of the type mentioned at the beginning and, on the other hand, to shorten the batch time and, optionally, the reaction time in accordance with the earlier applications cited above.

According to the invention, this problem is solved in a process of the type mentioned at the beginning by the fact that a heat transfer unit different from the reactor is used for heating and the heterogeneous catalyst is used in a fixed bed and in that the reaction mixture is continuously circulated in succession through the catalyst and then through the heat transfer unit.

In one particular embodiment of the invention, the heat transfer unit is a film evaporator, more especially a falling film evaporator or thin layer evaporator, in which the more readily volatile reaction products are separated. In this embodiment of the process, the reaction mixture after passing through the fixed-bed catalyst flows through the evaporator in which more readily volatile components are evaporated, so that the reaction equilibrium is shifted towards the product side. Thus, in an esterification reaction for example, the water of reaction formed may be removed directly after contact with the catalyst, i.e. immediately after its formation.

If the reaction is an esterification reaction catalyzed by ion exchangers containing sulfonic acid groups, possible hydrolysis of the sulfonic acid, i.e. elimination of the catalytically active acidic groups, is reduced or prevented in this way. Basically, however, any solid catalysts are suitable for the purposes of the invention. Thus, suitable catalysts are basic or acidic, organic or inorganic anion or cation exchangers or acidic aluminas or zeolite or specially prepared bleaching earths.

The coarse-particle catalyst material initially introduced into the fixed-bed catalyst is retained by suitable elements, for example by wedge-wire screens, and does not enter the stirred tank. The catalyst material may thus be reused for subsequent batches. Accordingly, there is no need to filter off a solid catalyst or to wash out a homogeneous catalyst.

To enhance the separation of the more readily volatile reaction product formed, the film evaporator is if necessary operated under reduced pressure.

In addition, the pressure in the film evaporator may advantageously be lowered during the production process, more especially beginning at normal pressure. Thus, the reaction equilibrium may be kept in a desired position in accordance with the progress of the reaction.

To obtain a better separating effect than that obtained with a film evaporator alone, educts and secondary products are not separated simply by distillation, instead a rectification column connected to the reactor, in which the more readily volatile reaction products are separated, is additionally used. In many cases, not only is the reaction product removed, at least one component of the starting product is also separated, so that the starting product has to be replenished accordingly. To avoid excessive replenishment, the more readily volatile components of the reaction mixture are rectified before their separation. This process is used, for example, in esterification reactions where an educt, for example a short-chain alcohol, is separated from a secondary product, for example water, by rectification to avoid the need to replenish the low-boiling educt, namely alcohol.

To prevent the reaction equilibrium from shifting, the starting products removed during separation of the more readily volatile reaction products are replenished.

It is particularly avantageous to use the process according to the invention for esterification and/or transesterification reactions. It is also particularly advantageous to use the process according to the invention for transacetalization and/or acetal-forming reactions, above all in the production of formaldehyde ethyl cyclododecyl acetal. This compound is known under the name of Boisambrene Forte® which is a registered trade mark. Where the process according to the invention is used for esterification or transesterification reactions, the production of wax esters or fragrances is particularly advantageous.

In reactions involving a pressure-dependent azeotrope between an educt and a reaction product, it is of advantage to carry out the reaction under the pressure at which maximum recycling of the educt can be guaranteed. In addition, it is proposed, particularly for the production of Boisambrene Forte® , that the reaction be carried out under an elevated pressure of up to 6 bar absolute and more especially up to 4 bar absolute. This is because the increase in pressure results in a reduction in the quantity of ethylal to be replenished in view of the dependence on pressure of the ethylal/ethanol azeotrope.

The invention also relates to a plant for the discontinuous heterogeneously catalyzed production of heat-sensitive products at elevated temperature comprising a reactor. To shorten the batch time and, optionally, the reaction time without creating additional problems during circulation of the reaction mixture, it is proposed that this plant be provided with a heat transfer unit arranged outside and connected to the reactor, a fixed-bed catalyst preceding the heat transfer unit and a pump for continuously circulating the reaction mixture in succession through the catalyst and then through the heat transfer unit.

The heat transfer unit is advantageously a film evaporator, more especially a falling film evaporator, which is designed to separate the more readily volatile reaction products in vacuo.

In addition, it is proposed that the catalyst container comprise elements for retaining catalyst material.

Further advantages mentioned above are obtained when the plant is designed to carry out the reaction under elevated pressure.

Examples of embodiment of the invention are described in detail in the following with reference to the accompanying drawings, wherein.

EXAMPLES

Example 1

Figure 1:
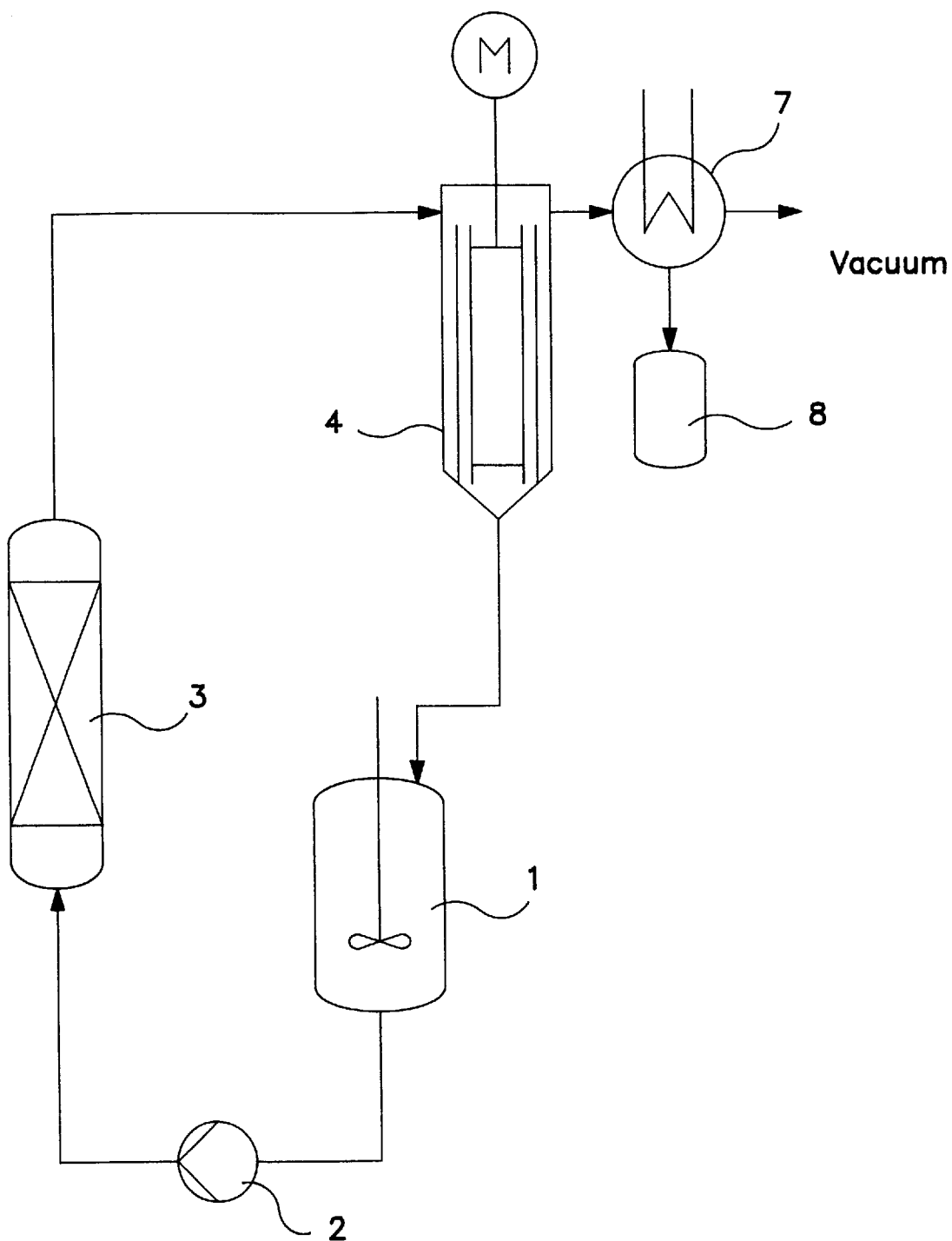
FIG. 1 shows a first embodiment comprising a thin layer evaporator and an external fixed catalyst bed.

Production of a wax ester from hexadecanoic acid and hexadecyl alcohol in the plant shown in FIG. 1.

739.5 g hexadecanoic acid (2.88 mol) and 706.4 g fatty alcohol (2.91 mol) are introduced into a heated stirred tank (1). A laboratory piston pump (2) transports the mixture through a heated glass vessel (3), the external fixed bed, into which 157 g of the strongly acidic ion exchanger resin Amberlite XE 365 (a product of Rohm and Haas) were introduced for catalysis at 130° C., to the thin layer evaporator (4) in which the water of reaction is removed by distillation. During the test, the pressure is reduced in steps from normal pressure to 20 mbar. The progress of the reaction is monitored through the acid content (AV) in the reaction mixture. After 5 hours, a conversion of 98.3%, based on the acid, is reached. 43 g distillate ($H_2O$) are collected in the distillate container (8), the remaining water being in the cold trap (7) preceding the vacuum pump.

"Amberlite® XE 365 is a strongly acidic ion exchange resin which is makroporous, with a porosity of 25%, contains the —$SO_3^+H^-$ group as the reactive group, has a surface area of 35 $m^2/g$, a particle size of from 0.3 to 1.2 mm, and a water content of about 55%."

Example 2

Figure 2:
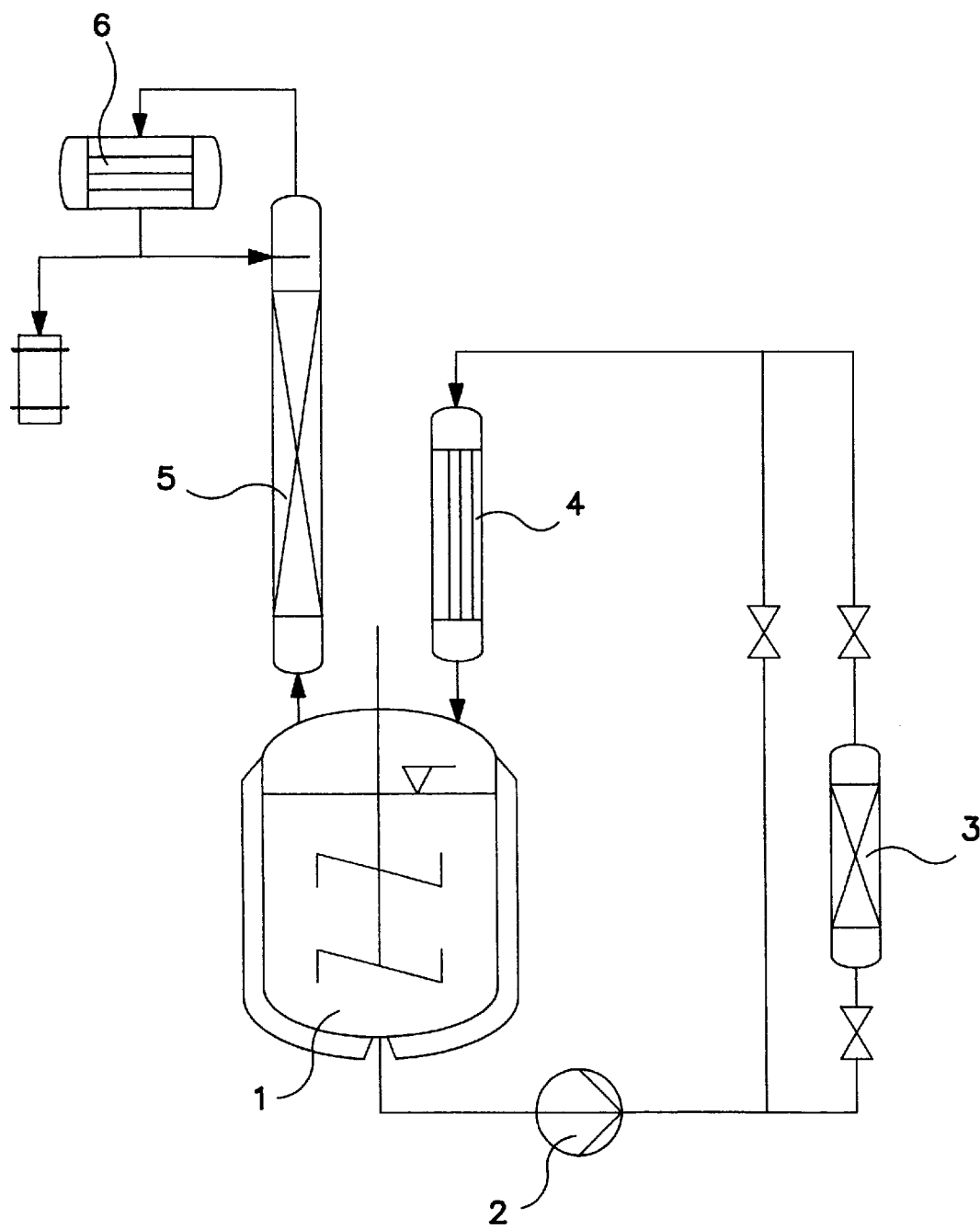
FIG. 2 shows a second embodiment of the plant according to the invention comprising an external fixed catalyst bed, a falling film evaporator and a rectification column, the latter being mounted on the reactor.

Production of formaldehyde ethyl cyclododecyl acetal (Boisambrene Forte®) (FIG. 2)

Formaldehyde ethyl cyclododecyl acetal is a fragrance for which the first production process was described in German patent 24 27 500; improved production processes were subsequently disclosed in patent applications DE-OS 30 30 543 and DE-OS 30 30 590.

In the original process, concentrated liquid acids are added or solid catalysts are stirred in for catalysis.

In the process according to the invention, the reactants cyclododecanol and ethylal are introduced in a molar ratio of 1:3 into a heatable stirred tank (1). A circulation pump (2) transports the reaction mixture through an external catalyst container (3), which is concurrently heated and contains the solid catalyst material. As in the known processes, the catalyst material used is either an acidified clay mineral (for example KSF, a product of Südchemie) or an acidic organic or inorganic cation exchanger. In contrast to the cited patents, however, the material used is in the form of coarse particles having a particle diameter of greater than 0.1 mm.

KSF is an acidified clay mineral composed of silicon dioxide, aluminum oxide, ferric oxide, magnesium oxide, calcium oxide, sodium oxide, and potassium oxide having a bulk density of 810±40 g/l, a surface area of about 10 $m^2/g$, a maximum moisture content of 10%, a pH in 10% suspension of about 1.5, and a free acid content as sulfuric acid of 155±25 mval/100 g.

The reaction mixture then flows through a falling film evaporator (4) in which the more volatile components (ethanol, ethylal) are partly evaporated. The vapors are concentrated to the azeotrope (approx. 40% by weight ethanol) in the rectification column (5) fitted to the reactor, condensed in the reflux condenser (6) and partly removed as distillate. The quantity of ethylal (chemical name: diethoxymethane or formaldehyde diethyl acetal) removed at the same time is replenished.

The reaction is carried out at boiling temperature, i.e. initially under normal pressure at approx. 90° C. and, towards the end of the reaction, at approx. 110° C.

After a reaction time of about 10 to 14 hours, a conversion of approximately 99%, based on cyclododecanol, is obtained for a yield of 80 to 85% ethyl cyclododecyl formal.

More particularly, Boisambrene Forte® is produced in accordance with the invention as follows:

140 g cyclododecanol and 238.4 g ethylal (diethoxymethane) are introduced into a heated laboratory stirred tank (1) (cf. FIG. 2). The catalyst container (3) contains 7 g of a montmorillonite catalyst (KSF/O Granulat, a product of Südchemie), composed of silicon dioxide, aluminum oxide, ferric oxide, magnesium oxide, calcium oxide, sodium oxide, and potassium oxide having a bulk density of 365±35 g/l, a surface area of 175±25 $m^2/g$, a maximum moisture content of 10%, a pH in 10% suspension of about 1.3, and a free acid content as sulfuric acid of 155±25 mval/100 g.

The reaction mixture is heated to 75° C. and then circulated through the catalyst container (3) by the laboratory pump (2). The temperature of the heating system for the stirred tank and falling film evaporator is slowly increased and, at a temperature of the reaction mixture of approximately 90° C., the first distillate accumulates at the head of the column (5). The reflux ratio at the head of the column is adjusted to 2 (1 s removal:2 s reflux). For every 15 ml distillate, 10 ml pure ethylal are replenished.

In just under 12 hours, a total of 90 ml distillate (ethanol/ethylal mixture) is thus removed from the reaction system and replaced by 60 ml pure ethylal. According to analysis by gas chromatography, the distillate accumulating contains approximately 37% ethanol.

The crude product formed is freed from residual ethylal/ethanol by distillation and, according to analysis by gas chromatography, contains 83.8% Boisambrene Forte® and 1.1% unreacted cyclododecanol. The remaining 15.1% consist essentially of dicyclododecyl formal and traces of secondary products.

List of Reference Numerals
reactor
circulation pump
catalyst container
heat transfer unit/falling film evaporator (FIG. 2) or
thin layer evaporator (FIG. 1)
rectification column
reflux condenser
condenser (cold trap)
distillate container

What is claimed is:

1. A discontinuous process for a heterogeneously catalyzed chemical reaction which is an esterification reaction, a transesterification reaction, a transacetalization reaction, or an acetal-forming reaction at an elevated temperature in which at least one heat-sensitive reaction product is formed comprising the steps of:

A. forming a reaction mixture of the components to be reacted in a reaction zone, B. passing the reaction mixture through a second zone containing a fixed-bed catalyst, C. passing the reaction mixture through a third zone in which the reaction mixture is heated to the desired reaction temperature and in which the more volatile reaction product or products are removed from the reaction mixture, and D. continuously circulating the reaction mixture in succession through the reaction zone, the second zone, and the third zone until the reaction has reached the desired degree of completion.

2. The process of claim 1 wherein the chemical reaction is an esterification or transesterification reaction.

3. The process of claim 1 wherein the chemical reaction is a transacetalization or acetal-forming reaction.

4. The process of claim 3 wherein the chemical reaction is for the production of formaldehyde ethyl cyclododecyl acetal.

5. The process of claim 4 wherein the reaction is carried out at a supraatmospheric pressure up to about 6 bar absolute.

6. The process of claim 5 wherein the pressure is up to about 4 bar absolute.

7. The process of claim 1 wherein in step D any starting materials that are removed from the reaction mixture together with volatile reaction products are separated from the volatile reaction products and returned to the reaction mixture.

8. The process of claim 1 wherein the third zone is a falling film evaporator or a thin layer evaporator.

9. The process of claim 1 wherein the process includes a fourth zone in which reaction products are separated from starting materials.

10. The process of claim 1 wherein step C is carried out under reduced pressure.

11. The process of claim 1 wherein the process is used for the preparation of a wax ester from hexadecanoic acid and hexadecyl alcohol.

* * * * *